(12) United States Patent
Burk et al.

(10) Patent No.: US 7,872,045 B2
(45) Date of Patent: *Jan. 18, 2011

(54) COMBINATION THERAPY FOR GLAUCOMA TREATMENT

(75) Inventors: Robert M. Burk, Laguna Beach, CA (US); Mark Holoboski, Laguna Niguel, CA (US); Scott M. Whitcup, Laguna Hills, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 1470 days.

This patent is subject to a terminal disclaimer.

(21) Appl. No.: 11/130,863

(22) Filed: May 16, 2005

(65) Prior Publication Data

US 2005/0209194 A1 Sep. 22, 2005

Related U.S. Application Data

(63) Continuation-in-part of application No. 10/672,499, filed on Sep. 26, 2003, now Pat. No. 6,956,057, which is a continuation of application No. 10/346,828, filed on Jan. 16, 2003, now Pat. No. 6,767,920, which is a continuation-in-part of application No. 09/882,720, filed on Jun. 14, 2001, now abandoned.

(51) Int. Cl.
*A61K 31/215* (2006.01)
*A61K 31/695* (2006.01)
(52) U.S. Cl. ........................ 514/530; 514/63
(58) Field of Classification Search .................. 514/546
See application file for complete search history.

(56) References Cited

U.S. PATENT DOCUMENTS

| 4,994,274 | A | 2/1991 | Chan et al. |
|---|---|---|---|
| 5,028,624 | A | 7/1991 | Chan et al. |
| 5,034,413 | A | 7/1991 | Chan et al. |
| 5,446,041 | A | 8/1995 | Chan et al. |
| 5,627,208 | A | 5/1997 | Stjernschantz et al. |
| 5,892,099 | A | 4/1999 | Maruyama et al. |
| 6,043,275 | A | 3/2000 | Maruyama et al. |
| 6,410,591 | B1 | 6/2002 | Burk |
| 2005/0209194 | A1 | 9/2005 | Burk et al. |

FOREIGN PATENT DOCUMENTS

| EP | 0292870 | 11/1988 |
|---|---|---|
| EP | 0737676 | 10/1996 |
| EP | 0 855 389 | 7/1998 |
| EP | 0860430 | 8/1998 |
| EP | 0 985 663 | 3/2000 |
| EP | 0 985 663 A1 | 3/2000 |
| JP | 09286775 A | 2/1998 |
| JP | 10-265454 | 10/1998 |
| JP | 2000-1472 | 1/2000 |
| WO | 0038663 | 7/2000 |
| WO | 0038667 | 7/2000 |
| WO | WO 00/38667 | 7/2000 |
| WO | WO 02/102389 | 12/2002 |
| WO | WO 02/102389 A1 | 12/2002 |
| WO | WO 03/047513 | 6/2003 |
| WO | WO 2006/058063 | 11/2005 |
| WO | WO 2006/055481 | 5/2006 |

OTHER PUBLICATIONS

Bito, L.Z., *Biological Protection with Prostaglandins*, Cohen, M.M., ed., Boca Raton, Fla, CRC Press Inc., 1985, pp. 231-252.
Bito, L.Z., *Applied Pharmacology in the Medical Treatment of Glaucomas*, Drance, S.M. and Neufeld, A.H. eds, New York, Grune & Stratton, 1984, pp. 477-505.
Nilsson et al, Invest. Ophthalmol. Vis. Sci. (suppl), 284 (1987).
Bito, L.Z., *Arch. Ophthalmol.* 105, 1036 (1987).
Siebold et al, *Prodrug* 5 3 1989.
Matsumura et al, "Prostaglandins having multi-substituted aryloxy groups and their use", Derwent Publications Ltd., (Sep. 29, 1998).
Dijkstra et al, Repertorium 96/97, p. 1089-1091.
Hirano et al, "Prostaglandin derivative", Derwent Publications Ltd., (Jun. 5, 2001).
Maruyama et al, "Design and synthesis of a highly selective EP4-receptor agonist", Bioorganic & Medicinal Chemistry Letters (2001), 2029-2031.
Kabashima, K, The Prostaglandin Receptor EP4 Suppresses Colitis, Mucosal Damage and CD4 Cell Activation in the Gut, Apr. 2002, pp. 883-893, vol. 109 The Journal of Clinical In.
Nitta, M. Expression of the EP4 Prostaglandin E2 Receptor Subtype with Rat Detran Sodium Sulphate Colitis: Colitis Suppression by a Selective Agonist, ONO-AE1-329, Blackwell.

*Primary Examiner*—Frederick Krass
*Assistant Examiner*—Adam Milligan
(74) *Attorney, Agent, or Firm*—Kevin J. Forrestal; John E. Wurst; Doina G. Ene

(57) ABSTRACT

A method is disclosed herein comprising administering a compound and a second drug to an eye of a mammal for the treatment of glaucoma or the reduction of intraocular pressure, said compound represented by the general formula I;

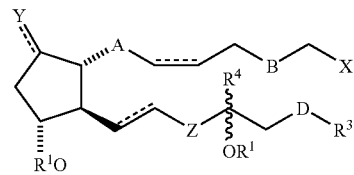

wherein A, B, D, X, Y, Z, $R^1$, $R^3$ and $R^4$ are as defined in the specification.

2 Claims, 2 Drawing Sheets

(SCHEME 1)

(SCHEME 2)

COMBINATION THERAPY FOR GLAUCOMA TREATMENT

CROSS REFERENCE TO RELATED APPLICATIONS

This patent application is a continuation in part of Ser. No. 10/672,499, filed Sep. 26, 2003, now U.S. Pat. No. 6,956,057 which is a continuation of Ser. No. 10/346,828, filed Jan. 16, 2003, now U.S. Pat. No. 6,767,920, which is a continuation in part of Ser. No. 09/882,720, filed Jun. 14, 2001, now abandoned.

BACKGROUND OF THE INVENTION

1. Field of the Invention

The present invention relates to 3, 7 or 3 and 7 thia or oxa prostanoic acid derivatives for the treatment of glaucoma or elevated intraocular pressure in combination with another drug.

2. Description of Related Art

Prostaglandins can be described as derivatives of prostanoic acid which have the following structural formula:

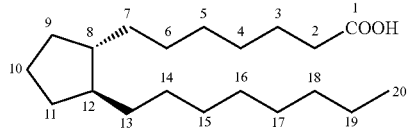

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins are useful for the long-term medical management of glaucoma (see, for example, Bito, L. Z. *Biological Protection with Prostaglandins*, Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505. Such prostaglandins include PGF2α, $PGF_{1\alpha}$, $PGE_2$, and certain lipid-soluble esters, such as $C_1$ to $C_2$ alkyl esters, e.g. 1-isopropyl ester, of such compounds.

EP 0 985 663 A1 discloses compounds such as the one shown below.

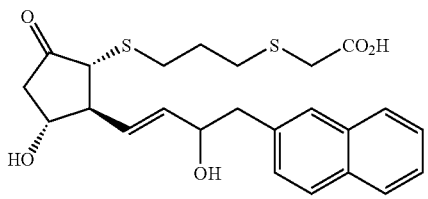

Inflammatory bowel disease (IBD) is a group of disease characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "EP4 works to keep mucosal integrity, to suppress the innate immunity, and to downregulate the proliferation and activation of CD4+ T cells. These findings have not only elucidated the mechanisms of IBD by NSAIDs, but also indicated the therapeutic potential of EP4-selective agonists in prevention and treatment of IBD." (Kabashima, et. al., The Journal of Clinical Investigation, April 2002, Vol. 9, 883-893)

SUMMARY OF THE INVENTION

Methods are disclosed herein comprising administering a compound and a second drug to an eye of a mammal for the treatment of glaucoma or the reduction of intraocular pressure said compound represented by the general formula I;

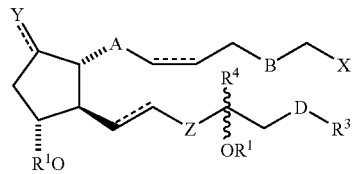

wherein hatched lines represent the α configuration, a triangle represents the β configuration, a wavy line represents either the α configuration or the β configuration and a dotted line represents the presence or absence of a double bond;

A and B are independently selected from the group consisting of O, S and $CH_2$; provided that at least one of A or B is S;

D represents a covalent bond or $CH_2$, O, S or NH;

X is $CO_2R$, $CONR_2$, $CH_2OR$, $P(O)(OR)_2$, $CONRSO_2R$, $SONR_2$ or

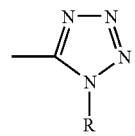

Y is O, OH, $OCOR^2$, halogen or cyano;

Z is $CH_2$ or a covalent bond;

R is H or $R^2$;

$R^1$ is H, $R^2$, phenyl, or $COR^2$;

$R^2$ is $C_1$-$C_5$ lower alkyl or alkenyl;

$R^3$ is benzothienyl, benzofuranyl, naphthyl, or substituted derivatives thereof, wherein the substituents maybe selected from the group consisting of $C_1$-$C_5$ alkyl, halogen, $CF_3$, CN, $NO_2$, $NR_2$, $CO_2R$ and OR; and, $R^4$ is hydrogen or $C_1$-$C_5$ alkyl.

Compositions, medicaments, and dosage forms related thereto are also disclosed.

BRIEF DESCRIPTION OF THE DRAWING FIGURES

DETAILED DESCRIPTION OF THE INVENTION

Figure 1:
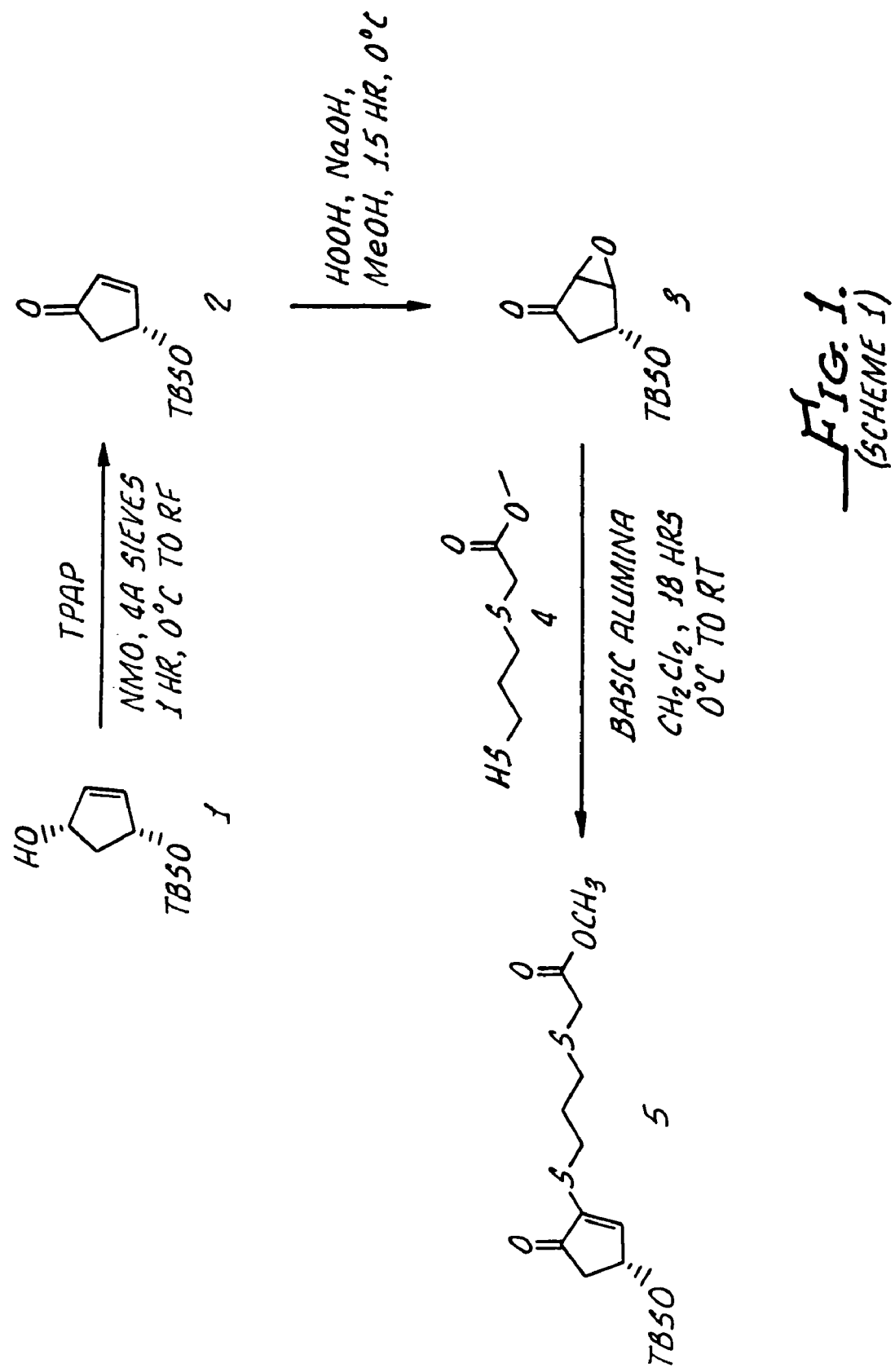
FIG. 1 is a schematic of the chemical synthesis of a certain intermediate for the compounds of the invention as disclosed in Examples 1 through 3.

The compounds used for the treatment of glaucoma in combination with other therapeutic agents are encompassed by the following structural formula I:

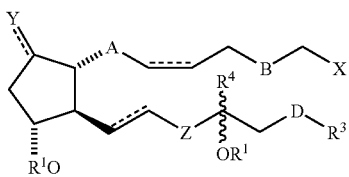

A preferred group of the compounds of the present invention includes compounds that have the following structural formula II:

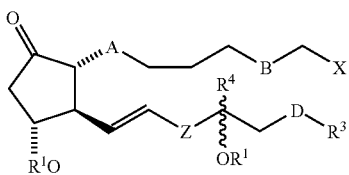

Another preferred group includes compounds having the formula III:

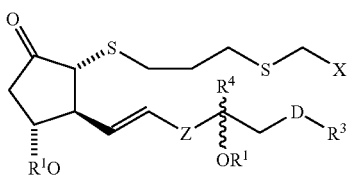

In the above formulae, the substituents and symbols are as hereinabove defined.

In the above formulae:
Preferably A and B are both S.
Preferably D represents a covalent bond or is $CH_2$; more preferably D is $CH_2$.
Preferably Z represents a covalent bond.
Preferably R is H.
Preferably $R^1$ is H.
Preferably $R^4$ is hydrogen or methyl, most preferably hydrogen.
Preferably Y=O.
Preferably X is $CO_2R$ and more preferably R is selected from the group consisting of H, methyl, i-propyl and n-propenyl.

The above compounds of the present invention may be prepared by methods that are known in the art or according to the working examples below. The compounds, below, are especially preferred representative, of the compounds of the present invention.

{3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid methyl ester, {3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid, {3-[(1R,2S,3R)-3-Hydroxy-2-((S)-(E)-3-(hydroxy)-5-(naphthyl)pent-1-enyl)-5-oxocyclopentylsulfanyl]propylsulfanyl}acetic acid isopropyl ester, {3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid methyl ester, {3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid, {3-[(1R,2S,3R)-3-Hydroxy-2-((S)-(E)-3-hydroxy-5-(benzothienyl)pent-1-enyl)-5-oxocyclopentylsulfanyl]propylsulfanyl}acetic acid isopropyl ester, {3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid methyl ester, {3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid, {3-[(1R,2S,3R)-3-Hydroxy-2-((S)-(E)-3-hydroxy-5-(benzofuranyl)pent-1-enyl)-5-oxocyclopentylsulfanyl]propylsulfanyl}acetic acid isopropyl ester, {3-[(1R,2S,3R)-3-Hydroxy-2-((E)-3-hydroxy-4-naphthalen-2-yl-but-1-enyl)-5-oxocyclopentylsulfanyl]propylsulfanyl}acetic acid methyl ester, {3-[(1R,2S,3R)-3-Hydroxy-2-((E)-3-hydroxy-4-naphthalen-2-yl-but-1-enyl)-5-oxocyclopentylsulfanyl]propylsulfanyl}acetic acid, {3-[(1R,2S,3R)-2-((E)-4-Benzo[b]thiophen-3-yl-3-hydroxybut-1-enyl)-3-hydroxy-5-oxocyclopentylsulfanyl]propylsulfanyl}acetic acid methyl ester, {3-[(1R,2S,3R)-2-((E)-4-Benzo[b]thiophen-3-yl-3-hydroxybut-1-enyl)-3-hydroxy-5-oxocyclopentylsulfanyl]propylsulfanyl}acetic acid, {3-[(1R,2S,3R)-3-Hydroxy-2-((S)-(E)-3-(hydroxy)-3-(methyl)-5-(naphthyl)pent-1-enyl)-5-oxocyclopentylsulfanyl]propylsulfanyl}acetic acid methyl ester, {3-[(1R,2S,3R)-3-Hydroxy-2-((E)-3-hydroxy-3-methyl-4-naphthalen-2-yl-but-1-enyl)-5-oxocyclopentylsulfanyl]propylsulfanyl}acetic acid methyl ester, {3-[(1R,2S,3R)-3-Hydroxy-2-((E)-3-hydroxy-3-methyl-4-naphthalen-2-yl-but-1-enyl)-5-oxocyclopentylsulfanyl]propylsulfanyl}acetic acid, {3-[(1R,2S,3R)-3-Hydroxy-2-((S)-(E)-3-(hydroxy)-3-(methyl)-5-(naphthyl)but-1-enyl)-5-oxocyclopentylsulfanyl]propylsulfanyl}acetic acid, {3-[(1R,2S,3R)-3-Hydroxy-2-((S)-(E)-3-(hydroxy)-3-(methyl)-5-(benzothienyl)pent-1-enyl)-5-oxocyclopentylsulfanyl]propylsulfanyl}acetic acid methyl ester and {3-[(1R,2S,3R)-3-Hydroxy-2-((S)-(E)-3-(hydroxy)-3-(methyl)-5-(benzothienyl)pent-1-enyl)-5-oxocyclopentylsulfanyl]propylsulfanyl}acetic acid methyl ester.

Second drugs useful for the treatment of glaucoma or other conditions include, but are not limited to.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof;

Prostaglandins including travoprost, UFO-21, chloprostenol, fluprostenol, 13,14-dihydro-chloprostenol, latanoprost and the like;

isopropyl unoprostone; and

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art. The compounds disclosed herein may be administered topically, periocularly, or by intraocular injection. Delivery may be by sustained release. For example, the drug may be delivered via a sustained release polymer, where the drug is released over time by diffusion of the drug from the polymer or degradation of the polymer. The polymer might be injected or implanted anywhere in or around the eye, including the subconjunctival or subtenons space.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For topical ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Those skilled in the art will readily understand that for oral or rectal administration the compounds of the invention are admixed with pharmaceutically acceptable excipients which per se are well known in the art. Specifically, a drug to be administered systemically, it may be confected as a powder, pill, tablet or the like, or as a syrup or elixir suitable for oral administration. Description of the substances normally used to prepare tablets, powders, pills, syrups and elixirs can be found in several books and treatise well known in the art, for example in Remington's Pharmaceutical Science, Edition 17, Mack Publishing Company, Easton, Pa.

Parenteral administration is generally characterized by injection. Injectables can be prepared in conventional forms, either as liquid solutions or suspensions, solid forms suitable for dissolving or suspending in liquid prior to injection, or as emulsions. Descriptions of substances and methods normally used to prepare formulations for parenteral administration can be found in several treatises and books well known in the art such as, Handbook On Injectable Drugs (11th edition), edited by Lawrence A. Trissel, (Chicago: Login Brothers Book Company; Jan. 15, 2001).

Figure 2:
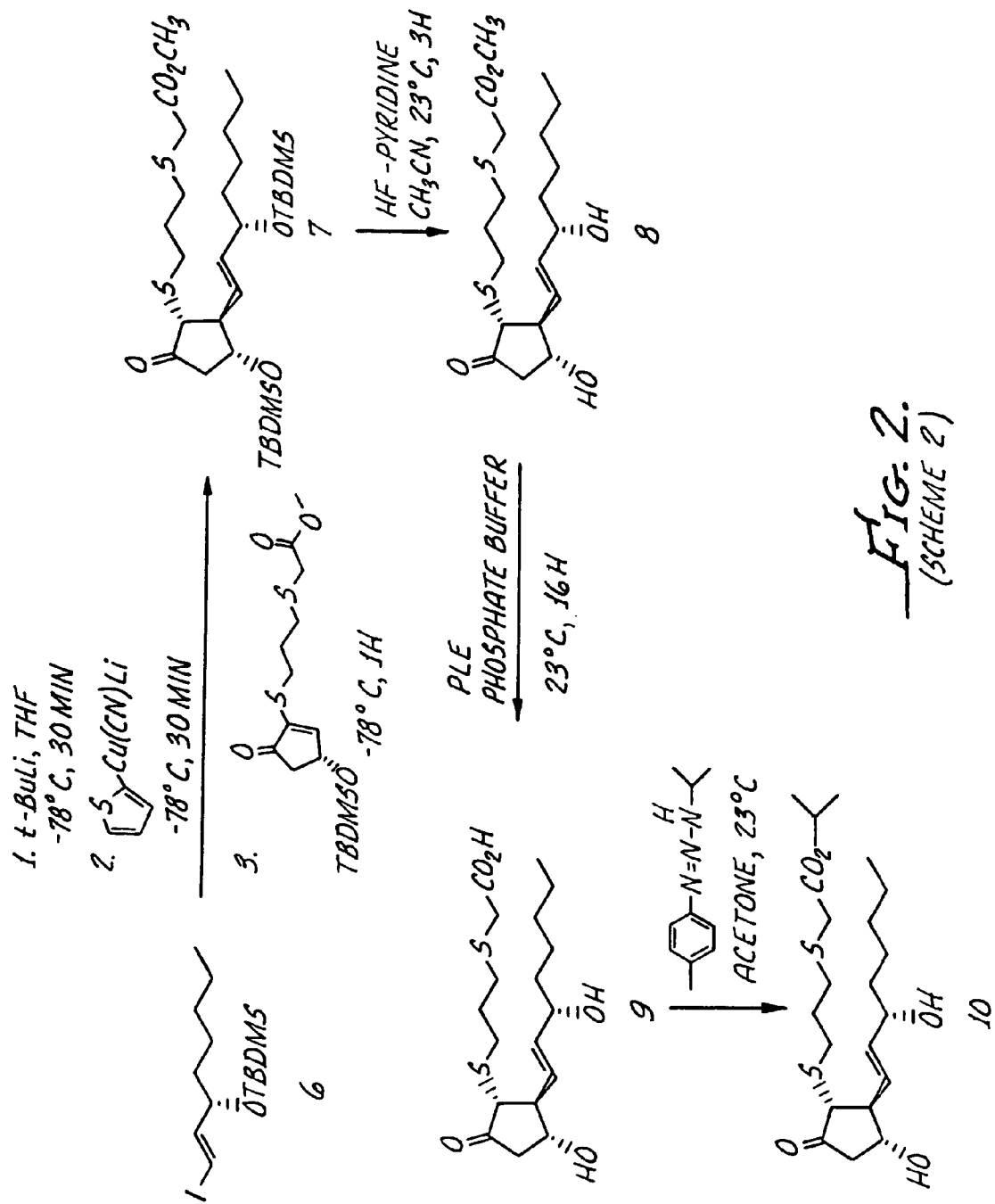
FIG. 2 is a schematic of the chemical synthesis of certain compounds related to the compounds of the invention as disclosed in Examples 4 through 7.

The invention is further illustrated by the following non-limiting Examples, which are summarized in the reaction schemes of FIGS. 1 and 2 wherein the compounds are identified by the same designator in both the Examples and the Figures.

EXAMPLE 1

(R)-4-(tert-Butyldimethylsilanyloxy)cyclopent-2-enone (2)

Tetrapropylammonium perruthenate (9.4 mg, 0.027 mmol) was added to a mixture of (1S,4R)-4-(tert-butyldimethylsilanyloxy)cyclopent-2-enol prepared, according to *Tetrahedron Letters*, Vol. 37, No. 18, 1996, pp. 3083-6, (118.6 mg, 0.54 mmol), 4-methylmorpholine N-oxide (94.9 mg, 0.81 mmol) and crushed 4 Å sieves (270 mg) in $CH_2Cl_2$ (10 mL). The mixture was stirred for 30 min and was passed through a plug of silica gel with $CH_2Cl_2$. The filtrate was concentrated in vacuo to give 100 mg (86%) of the above titled compound.

EXAMPLE 2

(R)-4-(tert-Butyldimethylsilanyloxy)-6-oxabicyclo[3.1.0]hexan-2-one (3)

Hydrogen peroxide (4.5 mL, 46.3 mmol, 30% wt. % solution in water) and 1N NaOH (46 µL, 0.046 mmol) were added to a solution of enone 2 (2.5 g, 11.5 mmol) in MeOH (30 mL) at 0° C. After stirring 1.5 h at 0° C. the mixture was concentrated in vacuo, washed with saturated aqueous $NH_4Cl$ and extracted with $CH_2Cl_2$ (3×). The combined organics were washed with brine, dried ($Na_2SO_4$), filtered and concentrated in vacuo to afford the above titled compound.

EXAMPLE 3

({3-[(R)-3-(tert-Butyldimethylsilanyloxy)-5-oxocyclopent-1-enylsulfanyl]propyl-sulfanyl}acetic acid methyl ester (5)

The epoxide 3 prepared above was diluted with $CH_2Cl_2$ (30 mL), (3-mercaptopropylsulfanyl)acetic acid methyl ester 4 (1.93 g, 10.7 mmol), prepared according to *Chem. Pharm. Bull.* 28 (2), 1980, 558-566, was added and the solution was cooled to 0° C. Basic alumina (11.9 g) was added and the reaction mixture was warmed to room temperature. After stirring for 18 h the mixture was filtered through celite and concentrated in vacuo. The residue was purified by flash column chromatography (silica gel, 6:1 hex/EtOAc) to yield 3.6 g (80%) of the above titled compound.

EXAMPLE 4

(3-{(1R,2S,3R)-3-(tert-Butyldimethylsilanyloxy)-2-[(S)-(E)-3-(tert-butyldimethylsilanoxy)oct-1-enyl]-5-oxocyclopentylsulfanyl}propylsulfanyl)acetic acid methyl ester (7)

tert-Butyllithium (1.47 mL of a 1.7M solution in pentane, 2.5 mmol) was added dropwise to a solution of tert-butyl[(S)-1-((E)-2-iodovinyl)hexyloxy]dimethylsilane 6 (462.5 mg, 1.25 mmol) in $Et_2O$ (6.0 mL) at −78° C. After stirring for 30 min lithium 2-thienylcyanocuprate (6.0 mL of a 0.25M solution in THF, 1.5 mmol) was added and the reaction was stirred an additional 30 min at −78° C. A solution of enone 5 (430 mg, 1.1 mmol) in $Et_2O$ (1 mL) was added and stirring was continued for an additional 1 h. The reaction mixture was then quickly poured into saturated aqueous $NH_4Cl$ cooled to 0° C. The mixture was extracted with EtOAc and the organic portion was washed with brine, dried ($Na_2SO_4$), filtered and concentrated in vacuo. The residue was quickly purified by flash column chromatography (silica gel, 100% hexane followed by 8:1 hex/EtOAc) to afford 270 mg (39%) of the above titled compound.

EXAMPLE 5

{3-[(1R,2S,3R)-3-Hydroxy-2-((S)-(E)-3-hydroxyoct-1-enyl)-5-oxocyclopentyl-sulfanyl]propylsulfanyl}acetic acid methyl ester (8)

Hydrogen fluoride-pyridine. (220 µL) was added to a solution of bis-TBDMS ether 7 (70 mg, 0.11 mmol) in $CH_3CN$ (2.0 mL) at 0° C. The reaction was warmed to room temperature, stirred 1 h, and recooled to 0° C. The reaction was quenched with saturated aqueous $NaHCO_3$ until gas evolution ceased. The mixture was extracted with $CH_2Cl_2$ (4×). The combined organics were washed with brine, dried ($Na_2SO_4$), filtered and concentrated in vacuo. Purification of the residue by flash column chromatography (silica gel, 100% $CH_2Cl_2$ followed by 30:1 $CH_2Cl_2$:MeOH) provided 40 mg (90%) of the above titled compound.

EXAMPLE 6

{3-[(1R,2S,3R)-3-Hydroxy-2-((S)-(E)-3-hydroxyoct-1-enyl)-5-oxocyclopentyl-sulfanyl]propylsulfanyl}acetic acid (9)

Methyl ester 8 (50 mg, 0.124 mmol) was dissolved in $CH_3CN$ (10 mL) and pH 7.2 phosphate buffer (3.0 mL) was added. The mixture was treated with PLE (400 µL, 1.34 mol/L) and stirred for 16 h at 23° C. The reaction mixture was extracted with EtOAc (3×). The combined organics were washed with brine, dried ($Na_2SO_4$), filtered and concentrated in vacuo. Purification of the residue by flash column chromatography (silica gel, 100% EtOAc) gave 5.3 mg (11%) of the above titled compound.

EXAMPLE 7

{3-[(1R,2S,3R)-3-Hydroxy-2-((S)-(E)-3-hydroxyoct-1-enyl)-5-oxocyclopentyl-sulfanyl]propylsulfanyl}acetic acid isopropyl ester (10)

Isopropyl-p-tolyltriazene (200 µL) was added dropwise to a solution of carboxylic acid 9 (10.5 mg, 0.026 mmol) in acetone (5.0 mL) at 23° C. After stirring for 1 h the reaction was quenched with 1N HCl and the solvent was removed in vacuo. The residue was extracted with $CH_2Cl_2$ (2×). The combined organics were dried ($Na_2SO_4$), filtered and concentrated in vacuo. Purification of the residue by flash column chromatography (silica gel, 4:1 hex/EtOAc) gave 4.3 mg (38%) of the above titled compound.

EXAMPLE 8

(3-{(1R,2S,3R)-3-(tert-Butyldimethylsilanyloxy)-2-
[(S)-(E)-3-(tert-butyldimethylsilanoxy)-5-(naphthyl)
pent-1-enyl]-5-
oxocyclopentylsulfanyl}propylsulfanyl)acetic acid
methyl ester (H)

(3-{(1R,2S,3R)-3-(tert-Butyldimethylsilanyloxy)-2-
[(S)-(E)-3-(tert-butyldimethylsilanoxy)-5-(naphthyl)
pent-1-enyl]-5-
oxocyclopentylsulfanyl}propylsulfanyl)acetic acid
methyl ester (L)

The named compound is prepared by substituting tert-butyl-[(E)-3-iodo-1-(2-naphthalen-2-yl-ethyl)allyloxy]dimethylsilane for tert-butyl[(S)-1-((E)-2-iodovinyl)hexyloxy]dimethylsilane in the method of Example 4. FCC gives a higher Rf compound and a lower Rf compound, designated as H and L, respectively.

EXAMPLE 9(H)

{3-[(1R,2S,3R)-3-Hydroxy-2-((S)-(E)-3-(hydroxy)-
5-(naphthyl)pent-1-enyl)-5-oxocyclopentylsulfanyl]
propylsulfanyl}acetic acid methyl ester (H)

The named compound is prepared by repeating the method of Example 5 with the named compound of Example 8 (H) rather then the named compound of Example 4.

EXAMPLE 9 (L)

{3-[(1R,2S,3R)-3-Hydroxy-2-((S)-(E)-3-(hydroxy)-
5-(naphthyl)pent-1-enyl)-5-oxocyclopentylsulfanyl]
propylsulfanyl}acetic acid methyl ester (L)

The named compound is prepared by repeating the method of Example 5 with the named compound of Example 8 (L) rather then the named compound of Example 4.

EXAMPLE 10 (H)

{3-[(1R,2S,3R)-3-Hydroxy-2-((S)-(E)-3-(hydroxy)-
5-(naphthyl)pent-1-enyl)-5-oxocyclopentylsulfanyl]
propylsulfanyl}acetic acid (H)

The named compound is prepared by repeating the method of Example 6 with the named compound of Example 9 (H) rather than the named compound of Example 5.

EXAMPLE 10 (L)

{3-[(1R,2S,3R)-3-Hydroxy-2-((S)-(E)-3-(hydroxy)-
5-(naphthyl)pent-1-enyl)-5-oxocyclopentylsulfanyl]
propylsulfanyl}acetic acid (L)

The named compound is prepared by repeating the method of Example 6 with the named compound of Example 9 (L) rather than the named compound of Example 5.

EXAMPLE 11

{3-[(1R,2S,3R)-3-Hydroxy-2-((S)-(E)-3-(hydroxy)-
5-(naphthyl)pent-1-enyl)-5-oxocyclopentylsulfanyl]
propylsulfanyl}acetic acid isopropyl ester The named compound is prepared by repeating the method of Example 7 with the named compound of Example 10 rather than the named compound of Example 6.

EXAMPLE 12

(3-{(1R,2S,3R)-3-(tert-Butyldimethylsilanyloxy)-2-
[(S)-(E)-3-(tert-butyldimethylsilanoxy)-5-(benzothienyl)pent-1-enyl]-5-
oxocyclopentylsulfanyl}propylsulfanyl)acetic acid
methyl ester (H)

(3-{(1R,2S,3R)-3-(tert-Butyldimethylsilanyloxy)-2-
[(S)-(E)-3-(tert-butyldimethylsilanoxy)-5-(benzothienyl)pent-1-enyl]-5-
oxocyclopentylsulfanyl}propylsulfanyl)acetic acid
methyl ester (L)

The named compound is prepared by substituting [(E)-1-(2-Benzo[b]thiophen-2-yl-ethyl)-3-iodoallyloxy]-ter-butyldimethylsilane for tert-butyl[(S)-1-((E)-2-iodovinyl)hexyloxy]dimethylsilane in the method of Example 4. FCC gives a higher Rf compound and a lower Rf compound, designated as H and L, respectively.

EXAMPLE 13(H)

{3-[(1R,2S,3R)-3-Hydroxy-2-((S)-(E)-3-hydroxy-5-
(benzothienyl)pent-1-enyl)-5-oxocyclopentylsulfanyl]propylsulfanyl}acetic acid methyl ester (H)

The named compound is prepared by repeating the method of Example 5 with the named compound of Example 12 (H) rather then the named compound of Example 4.

EXAMPLE 13(L)

{3-[(1R,2S,3R)-3-Hydroxy-2-((S)-(E)-3-hydroxy-5-
(benzothienyl)pent-1-enyl)-5-oxocyclopentylsulfanyl]propylsulfanyl}acetic acid methyl ester (L)

The named compound is prepared by repeating the method of Example 5 with the named compound of Example 12 (H) rather then the named compound of Example 4.

EXAMPLE 14(H)

{3-[(1R,2S,3R)-3-Hydroxy-2-((S)-(E)-3-hydroxy-5-
(benzothienyl)pent-1-enyl)-5-oxocyclopentylsulfanyl]propylsulfanyl}acetic acid (H)

The named compound is prepared by repeating the method of Example 6 with the named compound of Example 13 (H) rather than the named compound of Example 5.

EXAMPLE 14(L)

{3-[(1R,2S,3R)-3-Hydroxy-2-((S)-(E)-3-hydroxy-5-
(benzothienyl)pent-1-enyl)-5-oxocyclopentylsulfanyl]propylsulfanyl}acetic acid (L)

The named compound is prepared by repeating the method of Example 6 with the named compound of Example 13 (L) rather than the named compound of Example 5.

EXAMPLE 15

{3-[(1R,2S,3R)-3-Hydroxy-2-((S)-(E)-3-hydroxy-5-(benzothienyl)pent-1-enyl]-5-oxocyclopentylsulfanyl]propylsulfanyl}acetic acid isopropyl ester The named compound is prepared by repeating the method of Example 7 with the named compound of Example 14 rather than the named compound of Example 6.

EXAMPLE 16

(3-{(1R,2S,3R)-3-(tert-Butyldimethylsilanyloxy)-2-[(S)-(E)-3-(tert-butyldimethylsilanoxy)-5-(benzofuranyl)pent-1-enyl]-5-oxocyclopentylsulfanyl}propylsulfanyl)acetic acid methyl ester The named compound is prepared by substituting [(E)-1-(2-Benzo[b]furan-2-yl-ethyl)-3-iodoallyloxy]-tert-butyldimethylsilane for tert-butyl[(S)-1-((E)-2-iodovinyl)hexyloxy]dimethylsilane in the method of Example 4.

EXAMPLE 17

{3-[(1R,2S,3R)-3-Hydroxy-2-((S)-(E)-3-hydroxy-5-(benzofuranyl)pent-1-enyl]-5-oxocyclopentylsulfanyl]propylsulfanyl}acetic acid methyl ester The named compound is prepared by repeating the method of Example 5 with the named compound of Example 16 rather then the named compound of Example 4.

EXAMPLE 18

{3-[(1R,2S,3R)-3-Hydroxy-2-((S)-(E)-3-hydroxy-5-(benzofuranyl)pent-1-enyl]-5-oxocyclopentylsulfanyl]propylsulfanyl}acetic acid The named compound is prepared by repeating the method of Example 6 with the named compound of Example 17 rather than the named compound of Example 5.

EXAMPLE 19

{3-[(1R,2S,3R)-3-Hydroxy-2-((S)-(E)-3-hydroxy-5-(benzofuranyl)pent-1-enyl]-5-oxocyclopentylsulfanyl]propylsulfanyl}acetic acid isopropyl ester The named compound is prepared by repeating the method of Example 7 with the named compound of Example 18 rather than the named compound of Example 6.

EXAMPLE 20

(3-{(1R,2S,3R)-3-(tert-Butyldimethylsilanyloxy)-2-[(E)-3-(tert-butyldimethylsilanoxy)-4-naphthalen-2-yl-but-1-enyl]-5-oxocyclopentylsulfanyl}propylsulfanyl)acetic acid methyl ester (H)

(3-{(1R,2S,3R)-3-(tert-Butyldimethylsilanyloxy)-2-[(E)-3-(tert-butyldimethylsilanoxy)-4-naphthalen-2-yl-but-1-enyl]-5-oxocyclopentylsulfanyl}propylsulfanyl)acetic acid methyl ester (L)

The named compound is prepared by substituting tert-butyl-((E)-3-iodo-1-naphthalen-2-yl-methylallyloxy)-dimethylsilane for tert-butyl[(S)-1-((E)-2-iodovinyl)hexyloxy]dimethylsilane in the method of Example 4. FCC gives a higher Rf compound and a lower Rf compound, designated as H and L, respectively.

EXAMPLE 21 (H)

{3-[(1R,2S,3R)-3-Hydroxy-2-((E)-3-hydroxy-4-naphthalen-2-yl-but-1-enyl)-5-oxocyclopentylsulfanyl]propylsulfanyl}acetic acid methyl ester (H)

The named compound is prepared by repeating the method of Example 5 with the named compound of Example 20 (H) rather then the named compound of Example 4.

EXAMPLE 21(L)

{3-[(1R,2S,3R)-3-Hydroxy-2-((E)-3-hydroxy-4-naphthalen-2-yl-but-1-enyl)-5-oxocyclopentylsulfanyl]propylsulfanyl}acetic acid methyl ester (L)

The named compound is prepared by repeating the method of Example 5 with the named compound of Example 20 (H) rather then the named compound of Example 4.

EXAMPLE 22(H)

{3-[(1R,2S,3R)-3-Hydroxy-2-((E)-3-hydroxy-4-naphthalen-2-yl-but-1-enyl)-5-oxocyclopentylsulfanyl]propylsulfanyl}acetic acid (H)

The named compound is prepared by repeating the method of Example 6 with the named compound of Example 21 (H) rather than the named compound of Example 5.

EXAMPLE 22(L)

{3-[(1R,2S,3R)-3-Hydroxy-2-((E)-3-hydroxy-4-naphthalen-2-yl-but-1-enyl)-5-oxocycldpentylsulfanyl]propylsulfanyl}acetic acid (L)

The named compound is prepared by repeating the method of Example 6 with the named compound of Example 21 (H) rather than the named compound of Example 5.

EXAMPLE 23

{3-[(1R,2S,3R)-2-[(E)-4-Benzo[b]thiophen-3-yl-3-(tert-butyldimethylsilanyloxy)but-1-enyl]-3-(tert-butyldimethylsilanyloxy)-5-oxocyclopentylsulfanyl]propylsulfanyl}acetic acid methyl ester (H)

{3-[(1R,2S,3R)-2-[(E)-4-Benzo[b]thiophen-3-yl-3-(tert-butyldimethylsilanyloxy)but-1-enyl]-3-(tert-butyldimethylsilanyloxy)-5-oxocyclopentylsulfanyl]propylsulfanyl}acetic acid methyl ester (L)

The named compound is prepared by substituting ((E)-1-Benzo[b]thiophen-3-ylmethyl-3-iodo-allyloxy)-tert-butyldimethylsilane for tert-butyl[(S)-1-((E)-2-iodovinyl)hexyloxy]dimethylsilane in the method of Example 4. FCC gives a higher Rf compound and a lower Rf compound, designated as H and L respectively.

EXAMPLE 24(H)

{3-[(1R,2S,3R)-2-((E)-4-Benzo[b]thiophen-3-yl-3-hydroxybut-1-enyl)-3-hydroxy-5-oxocyclopentylsulfanyl]propylsulfanyl}acetic acid methyl ester (H)

The named compound is prepared by repeating the method of Example 5 with the named compound of Example 23 (H) rather then the named compound of Example 4.

EXAMPLE 24(L)

{3-[(1R,2S,3R)-2-((E)-4-Benzo[b]thiophen-3-yl-3-hydroxybut-1-enyl)-3-hydroxy-5-oxocyclopentylsulfanyl]propylsulfanyl}acetic acid methyl ester (L)

The named compound is prepared by repeating the method of Example 5 with the named compound of Example 23 (H) rather then the named compound of Example 4.

EXAMPLE 25(H)

{3-[(1R,2S,3R)-2-((E)-4-Benzo[b]thiophen-3-yl-3-hydroxybut-1-enyl)-3-hydroxy-5-oxocyclopentylsulfanyl]propylsulfanyl}acetic acid (H)

The named compound is prepared by repeating the method of Example 6 with the named compound of Example 24 (H) rather than the named compound of Example 5.

EXAMPLE 25(L)

{3-[(1R,2S,3R)-2-((E)-4-Benzo[b]thiophen-3-yl-3-hydroxybut-1-enyl)-3-hydroxy-5-oxocyclopentylsulfanyl]propylsulfanyl}acetic acid (L)

The named compound is prepared by repeating the method of Example 6 with the named compound of Example 24 (H) rather than the named compound of Example 5.

EXAMPLE 26

(3-{(1R,2S,3R)-3-(tert-Butyldimethylsilanyloxy)-2-[(S)-(E)-3-(tert-butyldimethylsilanoxy)-3-(methyl)-5-(naphthyl)pent-1-enyl]-5-oxocyclopentylsulfanyl}propylsulfanyl)acetic acid methyl ester (H)

(3-{(1R,2S,3R)-3-(tert-Butyldimethylsilanyloxy)-2-[(S)-(E)-3-(tert-butyldimethylsilanoxy)-3-(methyl)-5-(naphthyl)pent-1-enyl]-5-oxocyclopentylsulfanyl}propylsulfanyl)acetic acid methyl ester (L)

The named compound is prepared by substituting tert-Butyl-[(E)-3-iodo-1-methyl-1-(2-naphthalen-2-yl-ethyl)allyloxy]dimethylsilane for tert-butyl[(S)-1-((E)-2-iodovinyl)hexyloxy]dimethylsilane in the method of Example 4. FCC gives a higher Rf compound and a lower Rf compound, designated as H and L, respectively.

EXAMPLE 27(H)

{3-[(1R,2S,3R)-3-Hydroxy-2-((S)-(E)-3-(hydroxy)-3-(methyl)-5-(naphthyl)pent-1-enyl)-5-oxocyclopentylsulfanyl]propylsulfanyl}acetic acid methyl ester (H)

The named compound is prepared by repeating the method of Example 5 with the named compound of Example 26 (H) rather then the named compound of Example 4.

EXAMPLE 27(L)

{3-[(1R,2S,3R)-3-Hydroxy-2-((S)-(E)-3-(hydroxy)-3-(methyl)-5-(naphthyl)pent-1-enyl)-5-oxocyclopentylsulfanyl]propylsulfanyl}acetic acid methyl ester (L)

The named compound is prepared by repeating the method of Example 5 with the named compound of Example 26 (H) rather then the named compound of Example 4.

Example 28(H)

{3-[(1R,2S,3R)-3-Hydroxy-2-((S)-(E)-3-(hydroxy)-3-(methyl)-5-(naphthyl)pent-1-enyl)-5-oxocyclopentylsulfanyl]propylsulfanyl}acetic acid (H)

The named compound is prepared by repeating the method of Example 6 with the named compound of Example 27 (H) rather than the named compound of Example 5.

EXAMPLE 28(L)

{3-[(1R,2S,3R)-3-Hydroxy-2-((S)-(E)-3-(hydroxy)-3-(methyl)-5-(naphthyl)pent-1-enyl)-5-oxocyclopentylsulfanyl]propylsulfanyl}acetic acid (L)

The named compound is prepared by repeating the method of Example 6 with the named compound of Example 27(L) rather than the named compound of Example 5.

EXAMPLE 29

(3-{(1R,2S,3R)-3-(tert-Butyldimethylsilanyloxy)-2-[(E)-3-(tert-butyldimethylsilanoxy)-3-methyl-4-naphthalen-2-yl-but-1-enyl]-5-oxocyclopentylsulfanyl}propylsulfanyl)acetic acid methyl ester (H)

(3-{(1R,2S,3R)-3-(tert-Butyldimethylsilanyloxy)-2-[(E)-3-(tert-butyldimethylsilanoxy)-3-methyl-4-naphthalen-2-yl-but-1-enyl]-5-oxocyclopentylsulfanyl}propylsulfanyl)acetic acid methyl ester (L)

The named compound is prepared by substituting tert-butyl-[(E)-3-iodo-1-methyl-1-(2-naphthalen-2-yl-methyl)allyloxy]dimethylsilane for tert-butyl [(S)-1-((E)-2-iodovinyl)hexyloxy]dimethylsilane in the method of Example 4. FCC gives a higher Rf compound and a lower Rf compound, designated as H and L, respectively.

EXAMPLE 30(H)

{3-[(1R,2S,3R)-3-Hydroxy-2-((E)-3-hydroxy-3-methyl-4-naphthalen-2-yl-but-1-enyl)-5-oxocyclopentylsulfanyl]propylsulfanyl}acetic acid methyl ester (H)

The named compound is prepared by repeating the method of Example 5 with the named compound of Example 29 (H) rather then the named compound of Example 4.

EXAMPLE 30(L)

{3-[(1R,2S,3R)-3-Hydroxy-2-((E)-3-hydroxy-3-methyl-4-naphthalen-2-yl-but-1-enyl)-5-oxocyclopentylsulfanyl]propylsulfanyl}acetic acid methyl ester (L)

The named compound is prepared by repeating the method of Example 5 with the named compound of Example 29 (L) rather then the named compound of Example 4.

EXAMPLE 31(H)

{3-[(1R,2S,3R)-3-Hydroxy-2-((E)-3-hydroxy-3-methyl-4-naphthalen-2-yl-but-1-enyl)-5-oxocyclopentylsulfanyl]propylsulfanyl}acetic acid (H)

The named compound is prepared by repeating the method of Example 6 with the named compound of Example 30 (H) rather than the named compound of Example 5.

EXAMPLE 31(L)

{3-[(1R,2S,3R)-3-Hydroxy-2-((E)-3-hydroxy-3-methyl-4-naphthalen-2-yl-but-1-enyl)-5-oxocyclopentylsulfanyl]propylsulfanyl}acetic acid (L)

The named compound is prepared by repeating the method of Example 6 with the named compound of Example 30 (L) rather than the named compound of Example 5.

EXAMPLE 32

(3-{(1R,2S,3R)-3-(tert-Butyldimethylsilanyloxy)-2-[(S)-(E)-3-(tert-butyldimethylsilanoxy)-3-(methyl)-5-(benzylthienyl)pent-1-enyl]-5-oxocyclopentylsulfanyl}propylsulfanyl)acetic acid methyl ester (H)

(3-{(1R,2S,3R)-3-(tert-Butyldimethylsilanyloxy)-2-[(S)-(E)-3-(tert-butyldimethylsilanoxy)-3-(methyl)-5-(benzothienyl)pent-1-enyl]-5-oxocyclopentylsulfanyl}propylsulfanyl)acetic acid methyl ester (L)

The named compound is prepared by [(E)-1-(2-Benzo[b]thiophen-2-yl-ethyl)-3-iodo- 1-methylallyloxy]-tert-butyldimethylsilane for tert-butyl [(S)- 1 -((E)-2-iodovinyl)hexyloxy]dimethylsilane in the method of Example 4. FCC gives a higher Rf compound and a lower Rf compound, designated as H and L, respectively.

EXAMPLE 33(H)

{3-[(1R,2S,3R)-3-Hydroxy-2-((S)-(E)-3-(hydroxy)-3-(methyl)-5-(benzothienyl)pent-1-enyl)-5-oxocyclopentylsulfanyl]propylsulfanyl}acetic acid methyl ester (H)

The named compound is prepared by repeating the method of Example 5 with the named compound of Example 32 (H) rather then the named compound of Example 4.

EXAMPLE 33(L)

{3-[(1R,2S,3R)-3-Hydroxy-2-((S)-(E)-3-(hydroxy)-3-(methyl)-5-(benzothienyl)pent-1-enyl)-5-oxocyclopentylsulfanyl]propylsulfanyl}acetic acid methyl ester (L)

The named compound is prepared by repeating the method of Example 5 with the named compound of Example 32 (L) rather then the named compound of Example 4.

EXAMPLE 34(H)

{3-[(1R,2S,3R)-3-Hydroxy-2-((S)-(E)-3-(hydroxy)-3-(methyl)-5-(benzothienyl)pent-1-enyl)-5-oxocyclopentylsulfanyl]propylsulfanyl}acetic acid (H)

The named compound is prepared by repeating the method of Example 6 with the named compound of Example 33 (H) rather than the named compound of Example 5.

EXAMPLE 34(L)

{3-[(1R,2S,3R)-3-Hydroxy-2-((S)-(E)-3-(hydroxy)-3-(methyl)-5-(benzothienyl)pent-1-enyl)-5-oxocyclopentylsulfanyl]propylsulfanyl}acetic acid (L)

The named compound is prepared by repeating the method of Example 6 with the named compound of Example 33L rather than the named compound of Example 5.

The compounds of the Examples are subject to in vitro testing as described below. The results are reported in the table as IC50s in nM.

| Example No. | | $hEP_2$ | $hEP_3$ | $hEP_4$ |
|---|---|---|---|---|
| 33H | 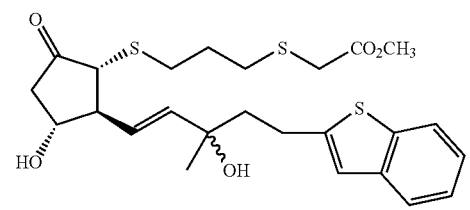 | NA | NA | 200 |

-continued
| Example No. | | hEP$_2$ | hEP$_3$ | hEP$_4$ |
|---|---|---|---|---|
| 33L | 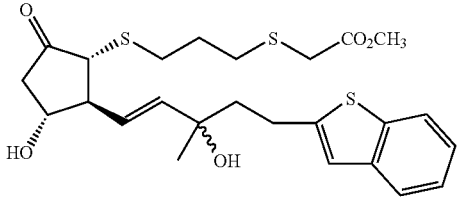 | NA | NA | 300 |
| 34H | 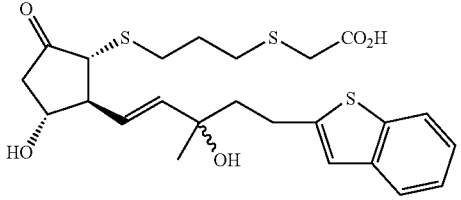 | >>$10^4$ | >$10^4$ | 32 |
| 34L | 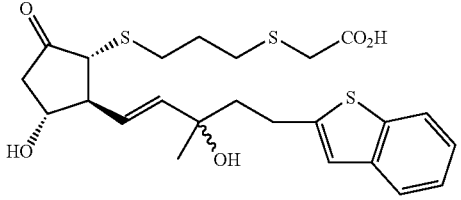 | NA | >$10^4$ | 68 |
| 13H | 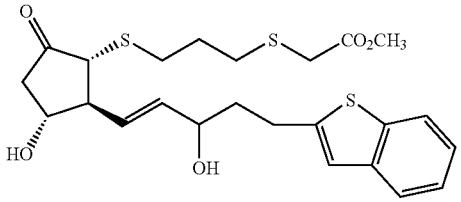 | NA | NA | 91 |
| 13L | 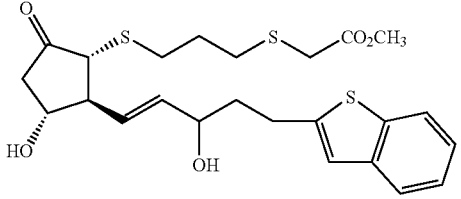 | >>$10^4$ | 7200 | 93 |
| 14H | 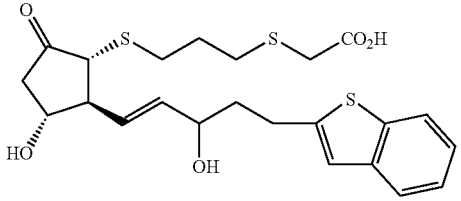 | >>$10^4$ | >$10^4$ | 27 |
| 14L | 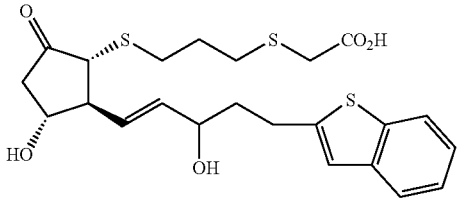 | $10^4$ | >$10^4$ | 13 |

-continued

| Example No. | | hEP$_2$ | hEP$_3$ | hEP$_4$ |
|---|---|---|---|---|
| 9H | *(structure)* | NA | NA | 40 |
| 9L | *(structure)* | NA | >10$^4$ | 40 |
| 10H | *(structure)* | >>10$^4$ | >10$^4$ | 450 |
| 10L | *(structure)* | >10$^4$ | 8300 | 19.5 |
| 27H | *(structure)* | NA | NA | 500 |
| 27L | *(structure)* | NA | NA | 3400 |
| 28H | *(structure)* | NA | >10$^4$ | 1700 |

-continued

| Example No. | Structure | hEP$_2$ | hEP$_3$ | hEP$_4$ |
|---|---|---|---|---|
| 28L | | NA | >10$^4$ | 1500 |
| 21H | | NA | >10$^4$ | 100 |
| 21L | | NA | >10$^4$ | 13 |
| 22H | | NA | >10$^4$ | 32 |
| 22L | | >>10$^4$ | >10$^4$ | 6.2 |
| 30H | | NA | >10$^4$ | 3100 |
| 30L | | NA | NA | 3200 |

| Example No. | | hEP$_2$ | hEP$_3$ | hEP$_4$ |
|---|---|---|---|---|
| 31H | 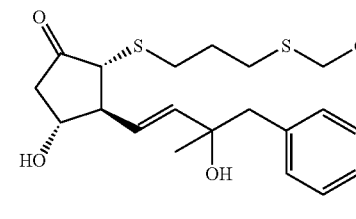 | NA | 8100 | 300 |
| 31L | 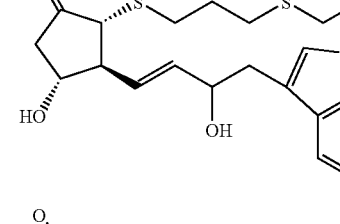 | NA | 9300 | 900 |
| 24H | 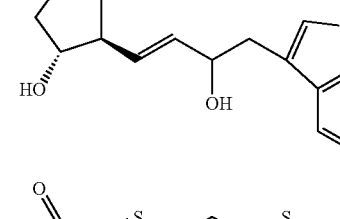 | NA | NA | 200 |
| 24L | 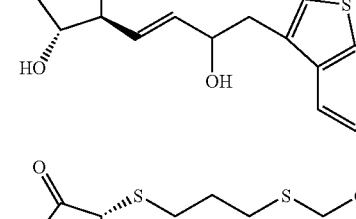 | 9300 | >10$^4$ | 30 |
| 25H | 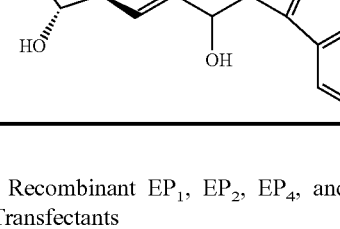 | >10$^4$ | NA | 69 |
| 25L | 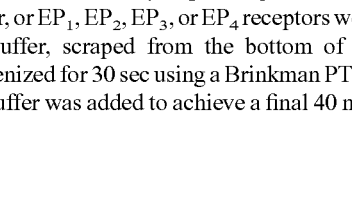 | 2200 | >10$^4$ | 5 |

Human Recombinant EP$_1$, EP$_2$, EP$_4$, and FP Receptors: Stable Transfectants HEK-293 cells stably expressing the human or feline FP receptor, or EP$_1$, EP$_2$, EP$_3$, or EP$_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM MgCl$_2$, 2M EDTA; ION HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl PGF$_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour. Non-specific binding was determined with 10 uM unlabeled 17-phenyl PGF$_{2\alpha}$.

[$^3$H-] PGE$_2$ (5 nM; specific activity 180 Ci mmol) was used as the radioligand for EP receptors. Binding studies employing EP$_1$, EP$_2$, EP$_3$, EP$_4$ were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Non-specific binding determined with $10^{-5}$M of unlabeled PGE$_2$,.

Plasmids encoding the human EP$_1$, EP$_2$, EP$_4$, and FP receptors were prepared by cloning the respective coding sequences into the eukaryotic expression vector pCEP4 (Invitrogen). The pCEP4 vector contains an Epstein Barr virus (EBV) origin of replication, which permits episomal replication in primate cell lines expressing EBV nuclear antigen (EBNA-1). Similarly, competitive experiments were caried out using [3H]17-phenylPGF$_{2\alpha}$ at 5 nM in the presence of test ligands at various concentrations. Also non-specific binding was, determined in the presence of excess unlabeled PGF$_{2\alpha}$ ($10^{-5}$ M).

It also contains a hygromycin resistance gene that is used for eukaryotic selection. The cells employed for stable transfection were human embryonic kidney cells (HEK-293) that were transfected with and express the EBNA-1 protein. These HEK-293-EBNA cells (Invitrogen) were grown in medium containing Geneticin (G418) to maintain expression of the EBNA-1 protein. HEK-293 cells were grown in DMEM with 10% fetal bovine serum (FBS), 250 µg ml G418 (Life Technologies) and 200 µg ml$^{-1}$ gentamicin or penicillin/streptomycin. Selection of stable transfectants was achieved with 200 µg m$^{-1}$ hygromycin, the optimal concentration being determined by previous hygromycin kill curve studies.

For transfection, the cells were grown to 50-60% confluency on 10 cm plates. The plasmid pCEP4 incorporating cDNA inserts for the respective human prostanoid receptor (20 µg) was added to 500 µl of 250 mM CaCl$_2$. HEPES buffered saline ×2 (2×HBS, 280 mM NaCl, 20 mM HEPES acid, 1.5 mM Na$_2$ HPO$_4$, pH 7.05-7.12) was then added dropwise to a total of 500 µl, with continuous vortexing at room temperature. After 30 min, 9 ml DMEM were added to the mixture. The DNA/DMEM/calcium phosphate mixture was then added to the cells, which had been previously rinsed with 10 ml PBS. The cells were then incubated for 5 hr at 37° C. in humidified 95% air/5% CO$_2$. The calcium phosphate solution was then removed and the cells were treated with 10% glycerol in DMEM for 2 min. The glycerol solution was then replaced by DMEM with 10% FBS. The cells were incubated overnight and the medium was replaced by DMEM/10% FBS containing 250 µg ml$^{-1}$ G418 and penicillin/streptomycin. The following day hygromycin B was added to a final concentration of 200 µg ml$^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use.

Human Recombinant EP$_3$ and TP Receptors: Transient Transfectants.

Plasmids encoding the human EP$_3$ (D isoform) or TP receptor were prepared by cloning the respective coding sequences into a pcDNA$_3$ vector (Invitrogen). COS-7 cells were transfected with pcDNA$_3$ containing cDNA encoding the EP$_3$ or TP receptor by employing the lipofectin method, according to the manufacturers instructions (Gibco). For radioligand binding studies, cells were harvested two days after transfection.

Radioligand Binding

Radioligand binding studies on plasma membrane fractions prepared from cells were performed as follows. Cells washed with TME buffer were scraped from the bottom of the plates and homogenized for 30 sec using a Brinkman PT 10/35 polytron. TME buffer was added as necessary to achieve a 40 ml volume in the centrifuge tubes. TME is comprised of 50 mM TRIS base, 10 mM MgCl$_2$, 1 mM EDTA; pH 7.4 is achieved by adding 1 N HCl. The cell homogenate was centrifuged at 19,000 rpm for 20-25 min at 4° C. using a Beckman Ti-60 or Tι-70 rotor. The pellet was then resuspended in TME buffer to provide a final protein concentration of 1 mg/ml, as determined by Bio-Rad assay. Radioligand binding assays were performed in a 100 µl or 200 µl volume.

The binding of [$^3$H] PGE$_2$ (specific activity 165 Ci/mmol) was determined in duplicate and, in at least 3 separate experiments. Incubations were for 60 min at 25° C. and were terminated by the addition of 4 ml of ice-cold 50 mM TRIS-HCl followed by rapid filtration through Whatman GF/B filters and three additional 4 ml washes in a cell harvester (Brandel). Competition studies were performed using a final concentration of 2.5 or 5 nM [H] PGE$_2$ and non-specific binding was determined with $10^{-5}$ M unlabelled PGE$_2$.

The binding of [$^3$H]-SQ29548 (specific activity 41.5 Ci mmol$^{-1}$) at TP receptors were determined in duplicate in at least three separate experiments. Radiolabeled SQ29548 was purchased from New England Nuclear. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 10 nM [$^3$H]-SQ 29548 and non-specific binding determined with 10 µM of the unlabeled prostanoid. For all radioligand binding studies, the criteria for inclusion were >50% specific binding and between 500 and 1000 displaceable counts or better.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A method comprising administering a compound and a second drug to an eye of a mammal for the treatment of glaucoma or the reduction of intraocular pressure, said compound being represented by the general formula I:

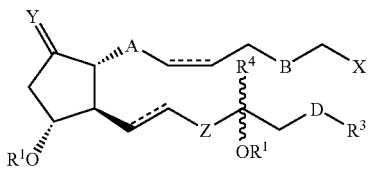

wherein the hatched lines represent the α configuration, a triangle represents the β configuration, a wavy line represents either the α or β configuration and a dotted line represents the presence or absence of a double bond;

A and B are S;
D represents a covalent bond;
X is $CO_2R$;
Y is O;
Z is a covalent bond;
R is H;
$R^1$ is H;
$R^3$ is benzothienyl and $R^4$ is hydrogen.

2. The method of claim 1 wherein said second drug is selected from the group consisting of β-blockers, adrenergic agonists, $α_2$-slective adrenergic agonists, carbonic anhydrase inhibitors, cholinertic agonists, glutamate antagonists, prostamides, prostagalandins, cannabinoids, and combinations thereof.

* * * * *